Figure 1A:
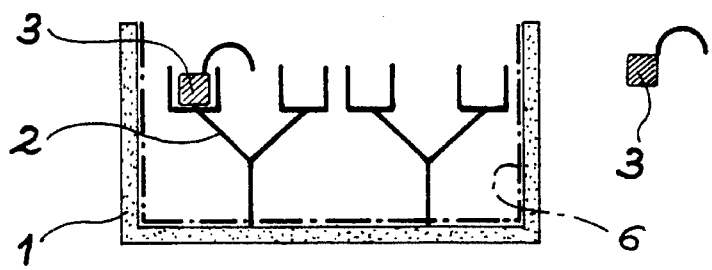

United States Patent [19]

Pradelles

[11] Patent Number: 5,476,770
[45] Date of Patent: Dec. 19, 1995

[54] IMMUNOMETRIC DETERMINATION OF AN ANTIGEN OR HAPTEN

[75] Inventor: Philippe Pradelles, Villebon, France

[73] Assignee: Commissariat A L'Energie Atomique, Paris, France

[21] Appl. No.: 184,935

[22] Filed: Jan. 24, 1994

[30] Foreign Application Priority Data

Jan. 28, 1993 [FR] France ................................ 93 00869

[51] Int. Cl.⁶ ...................... G01N 33/545; G01N 33/577
[52] U.S. Cl. .................... 435/7.94; 435/7.5; 436/500; 436/518; 436/531; 436/817; 436/822
[58] Field of Search ........................... 435/7.5, 7.9, 7.92, 435/7.94, 962, 969, 971; 436/518, 543, 500, 531, 817, 822

[56] References Cited

U.S. PATENT DOCUMENTS

| | | | |
|---|---|---|---|
| 4,376,110 | 3/1983 | David et al. ............................ | 436/513 |
| 4,703,001 | 10/1988 | Vodian et al. . | |
| 4,794,090 | 12/1988 | Parham et al. ......................... | 436/531 |
| 5,236,830 | 8/1993 | Ishikawa .................................. | 435/7.5 |

FOREIGN PATENT DOCUMENTS

| | | |
|---|---|---|
| 0080109 | 6/1983 | European Pat. Off. . |
| 0467078 | 1/1992 | European Pat. Off. . |
| WO91/16377 | 10/1991 | WIPO . |

OTHER PUBLICATIONS

Creighton, T. E. Protein Function. IRL Press at Oxford University Press, 1989. pp. 14–16.
Harlow, E. Antibodies: A Laboratory Manual. Cold Spring Harbor, N.Y.: Cold Spring Harbor Laboratory, 1988. pp. 26–28.
Pradelles, P., et al. "Immunometric Assay of Low Molecular Weight Haptens Containing Primary Amino Groups". Analytical Chemistry, 66:16–22, 1994.
Ikegaki, N., et al. "Gluteraldehyde fixation of the primary antibody–antigen complex on nitrocellulose paper increases the overall sensitivity of immunoblot assay." Journal of Immunological Methods, 124:205–210, 1989.

Primary Examiner—Mary E. Ceperley
Attorney, Agent, or Firm—Oblon, Spivak, McClelland, Maier & Neustadt

[57] ABSTRACT

The invention relates to a process for the immunometric determination of an antigen or hapten.

According to this process, contacting takes place (FIG. 1A) between the antigen or hapten (3) to be determined and the antibodies (2) fixed to a solid phase in order to immunologically bond the antigen or hapten with the antibody. This is followed (FIG. 1B) by immobilizing the antigen or hapten (3) by a covalent bond (4) to the solid phase (1) whilst releasing its epitope (FIG. 1C). This is followed by the contacting thereof (FIG. 1D) with labelled antibodies (5) and determination takes place (FIG. 1E) of the quantity of fixed labelled antibodies in order to deduce therefrom the initial hapten or antigen concentration.

As a result of this stage of immobilizing and releasing the epitope, a high sensitivity is obtained using a single antibody.

12 Claims, 5 Drawing Sheets

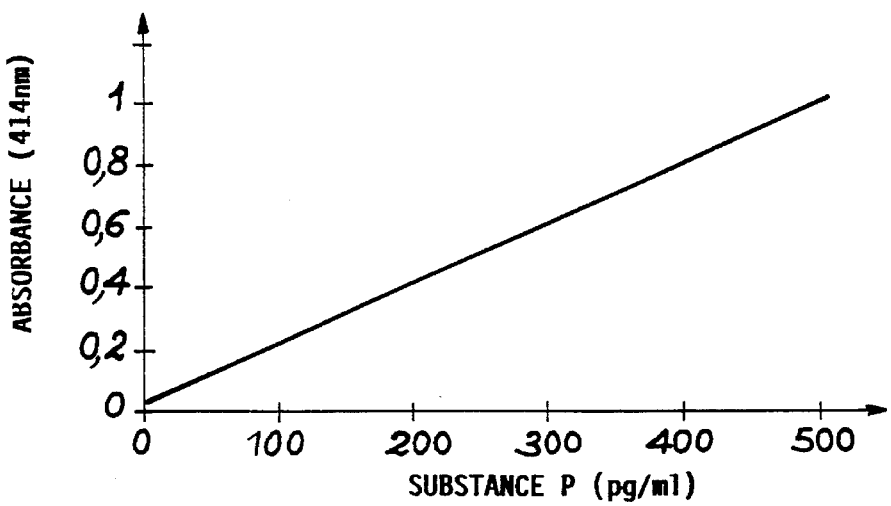
FIG. 2
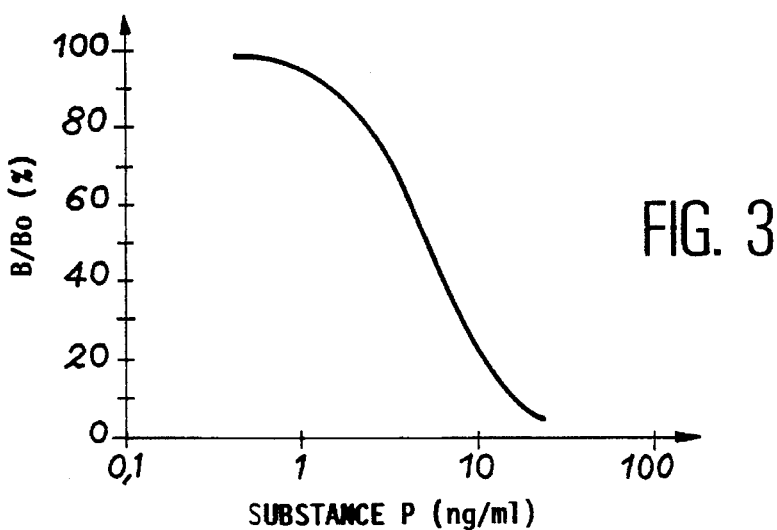
FIG. 3
FIG. 4
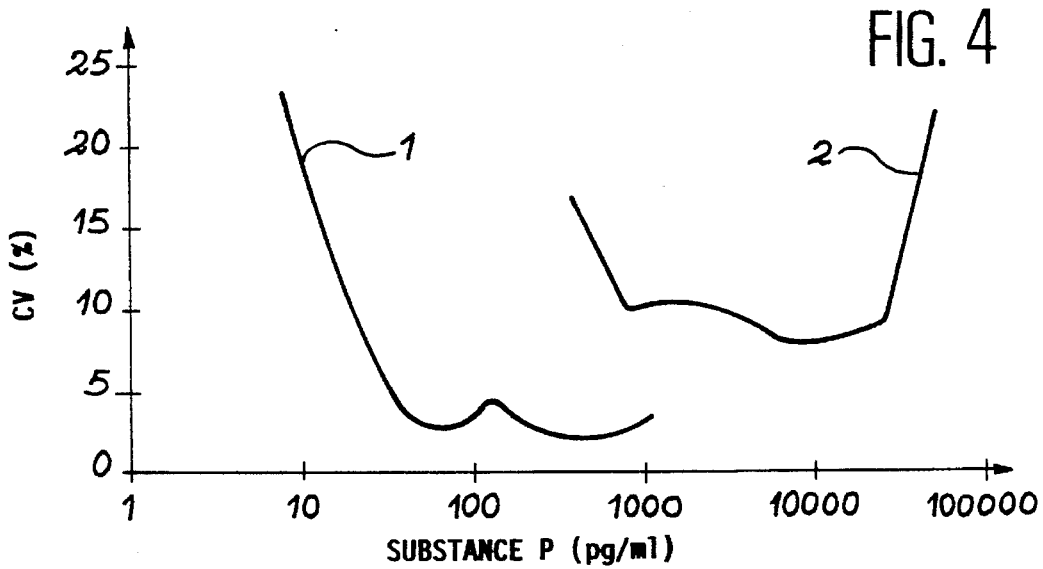

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:1:

```
Arg  Pro  Val  Lys  Val  Tyr  Pro  Asn  Gly  Ala  Glu  Asp  Glu  Ser  Ala  Glu
 1              5                        10                       15
Ala  Phe  Pro  Leu  Glu  Phe
               20
```

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:2:

```
Asp  Arg  Val  Tyr  Ile  His  Pro  Phe
 1              5
```

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:3:

```
Ser  Leu  Arg  Arg  Ser  Ser  Cys  Phe  Gly  Gly  Arg  Met  Asp  Arg  Ile  Gly
 1              5                        10                       15
Ala  Gln  Ser  Gly  Leu  Gly  Cys  Asn  Ser  Phe  Arg  Tyr
               20                       25
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:4:

```
Arg  Pro  Pro  Gly  Phe  Ser  Pro  Phe  Arg
 1              5
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:5:

```
Tyr  Gly  Gly  Phe  Met
 1              5
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 10
        ( D ) OTHER INFORMATION: /note="C-terminal amide"

( x i ) SEQUENCE DESCRIPTION: SEQ ID NO:6:

Tyr His Trp Ser Tyr Gly Leu Arg Pro Gly
    1               5                   10

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 9
        ( D ) OTHER INFORMATION: /note="C-terminal amide"

( x i ) SEQUENCE DESCRIPTION: SEQ ID NO:7:

Cys Tyr Ile Gln Asn Cys Pro Leu Gly
    1               5

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 10
        ( D ) OTHER INFORMATION: /note="C-terminal amide"

( x i ) SEQUENCE DESCRIPTION: SEQ ID NO:8:

Cys Tyr Phe Gln Asn Cys Cys Pro Arg Gly
    1               5                   10

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 10
        ( D ) OTHER INFORMATION: /note="C-terminal amide"

( x i ) SEQUENCE DESCRIPTION: SEQ ID NO:9:

His Lys Thr Asp Ser Phe Val Gly Leu Met

```
                1               5                      1 0
```

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 10
        ( D ) OTHER INFORMATION: /note="C-terminal amide"

( x i ) SEQUENCE DESCRIPTION: SEQ ID NO:10:

```
    Asp  Met  His  Asp  Phe  Phe  Val  Gly  Leu  Met
    1                   5                        1 0
```

( 2 ) INFORMATION FOR SEQ ID NO:11:

( i ) SEQUENCE CHARACTERISTICS:
        ( A ) LENGTH: 21 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:11:

```
    Cys  Ser  Cys  Ser  Ser  Leu  Met  Asp  Lys  Glu  Cys  Val  Tyr  Phe  Cys  His
    1                   5                        1 0                       1 5

Leu  Asp  Ile  Ile  Trp
                        2 0
```

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 11
        ( D ) OTHER INFORMATION: /note="C-terminal amide"

( x i ) SEQUENCE DESCRIPTION: SEQ ID NO:12:

```
    Arg  Pro  Lys  Pro  Gln  Gln  Phe  Phe  Gly  Leu  Met
    1                   5                        1 0
```

IMMUNOMETRIC DETERMINATION OF AN ANTIGEN OR HAPTEN

The present invention relates to a process for the immunometric determination of a substance constituted by an antigen or a hapten.

It is more particularly applicable to the determination of haptens, i.e. small molecules which very frequently in themselves only have a single fixing site (monoepitopic haptens). Thus, a hapten is a small molecule, which cannot in itself stimulate the synthesis of antibodies, but which can induce the formation of antibodies when it is coupled with a protein, which serves as the antigen carrier.

In the case of haptens whose size is not adequate to be simultaneously bonded to two antibodies, conventionally immunological determinations take place by competition between the hapten to be determined and the same labelled hapten, for antibody sites in limited quantities, fixed to a solid phase, optionally by means of another antibody, as described by Pradelles et al in Anal. Chem. 57, 1985, p 1170 and by Renzi et al in Trends in Cluster Headache, F. Sicuteri et al, Editors, Elsevier, N.Y., 1987, pp 125–134, in the case of the P substance.

Other immunological determinations such as immunometric determinations of the sandwich type or having two sites, in which the antigen is fixed to a solid phase by means of a first antibody and then identified by a second labelled antibody and brought into excess, make it possible to obtain a much greater sensitivity, but they are unfortunately not applicable to monoepitopic haptens.

The present invention specifically relates to an immunometric determination process more particularly usable for the determination of these haptens, which makes it possible to obtain a better sensitivity than determinations by competition.

According to the invention, the process for the immunometric determination of a substance constituted by an antigen or a hapten is characterized in that it comprises the following stages:

1) contacting a sample containing the substance to be determined with a solid phase on which are fixed a saturation substance and a capture antibody, called the first antibody, which is specific to an epitope of the substance to be determined, in order to immunologically bond the substance to be determined to the fixed antibody, 2) subjecting the solid phase on which are fixed the saturation substance, the antibody and the substance to be determined to a treatment by means of at least one reagent in order to immobilize the substance to be determined on the solid phase by the formation of covalent bonds and in order to make accessible an epitope of the substance to be determined with a view to a further immunological reaction, 3) contacting the thus treated solid phase with a labelled antibody, called the second antibody, which is specific to the substance to be determined, 4) measuring the quantity of the second antibody fixed to the solid phase and 5) determining on a calibration curve the quantity of the substance to be determined which is present in the sample on the basis of the quantity of the second antibody measured in the fourth stage.

In this process, the treatment performed in the second stage is very important, because it leads to a complete immobilization of the substance to be determined on the solid phase by covalent chemical bonds and to a restoration of the immunological properties of the substance to be determined so that it can again react immunologically with an antibody.

Generally, this treatment comprises a first stage in which the substance to be determined and which is immunologically bonded to the first antibody is reacted with an at least bifunctional reagent able to form covalent bonds on the one hand with the substance to be determined and on the other with the solid phase coated with the first antibody and the saturation substance in order to immobilize the substance to be determined on the solid phase by means of said reagent and a second stage in which the substance to be determined immobilized on the solid phase undergoes a treatment for the denaturation of its immunological bond with the first antibody.

The bifunctional reagent used in the first stage is a reagent having a first functional group able to chemically react with the solid phase, the saturation substance and/or the first antibody fixed to the solid phase, and a second functional group, identical to or different from the first, able to react with the substance to be determined. These functional groups can e.g. be anine groups, acid groups, aldehyde groups, thyrosyl groups, histidyl groups or thiol groups.

When these functional groups are identical, there is a homobifunctional or homopolyfunctional reagent. Examples of such reagents are glutaraldehyde, difluorodinitrobenzene, disuccinimidyl suberate, bis(maleimido)-hexane and bis[β-(4-azido-salicylamido)-ethyl]-disulphide.

When the functional groups are different, there is a heterobifunctional or heteropolyfunctional reagent. Examples of such reagents are N-succinimidyl-3-(2-pyridyldithio)-propionate and succinimidyl-4-(N-maleimidomethyl)-cyclohexane-1-carboxylate.

The choice of the reagent used not only depends on the substance to be determined, but also on the solid phase and the antibody used.

The solid phase can be constituted by the solid phases generally used in immunological determinations, e.g. microtitration plates, tubes, membranes made from a plastics material, e.g. polystyrene, nitrocellulose or polyester, glass balls, or any random substance able to covalently or non-covalently, directly or non-directly fix the first antibody. Fixing can take place by adsorption, covalent chemical bonding or by means of bonding molecules such as antibodies and the avidin-biotin system. It is also possible to use solid phases in mineral materials such as hydroxylapatite, mullite, alumina, $ZrO_2$ and $Ca_3(PO_4)_2$.

The fixing of the first antibody to the surface of the solid phase can be passive or active. It can be obtained by direct adsorption or by means of appropriate reagents.

In the process of the invention, the first and second antibodies used are both specific antibodies of the substance to be determined. Said first and second antibodies can come from the same source or different sources. Moreover, these antibodies can be polyclonal antibodies or monoclonal antibodies.

In the case where the substance to be determined is a monoepitopic hapten, the first and second antibodies are identical and preferably monoclonal.

In the case where the substance to be determined is an antigen, it is possible to use two different antibodies, but it is advantageous to use two identical antibodies and preferably monoclonal antibodies. For the second labelled or marked antibody, marking can take place by means of various methods, e.g. a radioactive element, an enzyme, a fluorescent marker, a luminescent marker, or molecules able to react with avidin or streptavidin, such as biotin and its structural analogs.

When the second antibody is marked or labelled by means of a molecule such as an enzyme, a fluorescent maker, a luminescent marker or a molecule able to react with avidin or streptavidin, the coupling of the marker to the antibody can take place by conventional methods normally used in such determinations.

The process according to the invention can be advantageously applied to the determination of antigens because, in this case, it is possible to obtain the same sensitivity as with sandwich-type determinations whilst using a single antibody and preferably a monoclonal antibody.

However, the process according to the invention has an even greater interest for the determination of monoepitopic haptens, because it makes it possible to in this case obtain much greater sensitivities than in determinations by competition, using a single antibody, taking advantage of the use of reagents in excess (capture antibody and labelled antibodies), as takes place with two-site immunometric determinations.

As examples of haptens which can be determined by the process according to the invention, reference can be made to ACTH, angiotensin, ANF, bradykinin, encephalin, LHRH, oxytocin, vasopressin, neurokinins, endotheline, substance P, thyroxine and leucotriene $E_4$.

The formulas of these haptens are given hereinafter:

ACTH(18-39)(SEQ ID NO:1): Arg-Pro-Val-Lys-Val-Tyr-Pro-Asn-Gly-Ala-Glu-Asp-Glu-Ser-Ala-Glu-Ala-Phe-Pro-Leu-Glu-Phe

ANGIOTENSIN II(SEQ ID NO:2): Asp-Arg-Val-Tyr-Ile-His-Pro-Phe

ANF(1-28)(SEQ ID NO:3): Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr

BRADYKININ(SEQ ID NO:4): Arg-Pro-Pro-Gly-Phe-Ser-Pro-Phe-Arg

ENCEPHALIN(SEQ ID NO:5): Tyr-Gly-Gly-Phe-Met

LHRH(SEQ ID NO:6): Pyr-His-Trp-Ser-Tyr-Gly-Leu-Arg-Pro-Gly-NH2

OXYTOCIN(SEQ ID NO:7): Cys-Tyr-Ile-Gln-Asn-Cys-Pro-Leu-Gly-NH2

VASOPRESSIN(SEQ ID NO:8): Cys-Tyr-Phe-Gln-Asn-Cys-Cys-Pro-Arg-Gly-$NH_2$

NEUROKININ A(SEQ ID NO:9): His-Lys-Thr-Asp-Ser-Phe-Val-Gly-Leu-Met-$NH_2$

NEUROKININ B(SEQ ID NO:10): Asp-Met-His-Asp-Phe-Phe-Val-Gly-Leu-Met-$NH_2$

ENDOTHELINE(SEQ ID NO:11): Cys-Ser-Cys-Ser-Ser-Leu-Met-Asp-Lys-Glu-Cys-Val-Tyr-Phe-Cys-His-Leu-Asp-Ile-Ile-Trp

SUBSTANCE P(SEQ ID NO:12): Arg-Pro-Lys-Pro-Gln-Gln-Phe-Phe-Gly-Leu-Met-$NH_2$

THYROXINE:

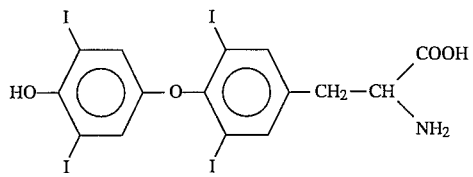

Other features and advantages of the invention can be gathered from the following illustrative and non-limitative description and with reference to the attached drawings, wherein show:

FIGS. 1A to 1E Diagrammatic representations of the different stages of the immunometric determination process according to the invention.

FIG. 2 A calibration curve obtained for the immunometric determination of the substance P by the process according to the invention.

FIG. 3 A calibration curve obtained for the determination by competition of the substance P by a prior art process.

FIG. 4 A diagram illustrating the precision profiles obtained for the substance P with the immunometric determination according to the invention and the prior art competition determination.

Figure 5:
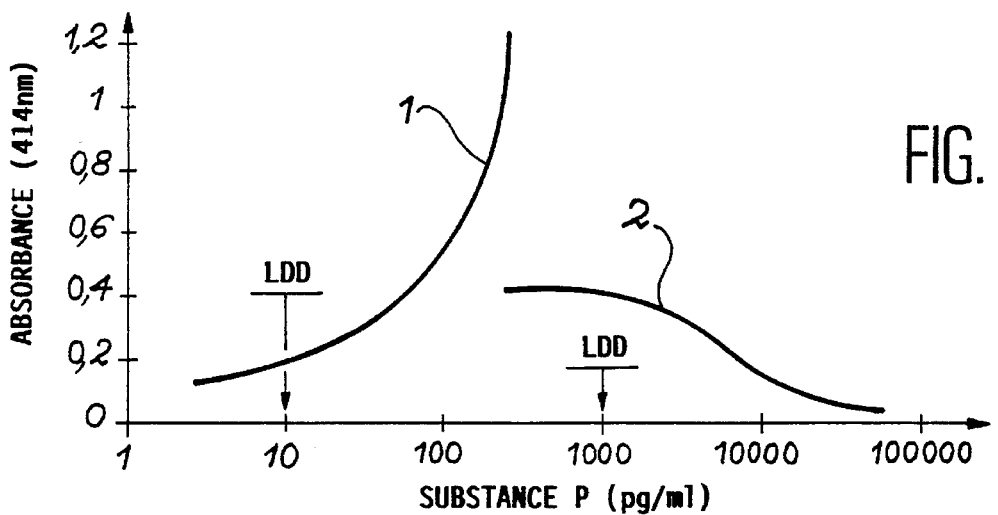

FIG. 5 A diagram illustrating the sensitivities of the determinations of the substance P by the process of the invention and the prior art process.

Figure 6:

FIG. 6 A diagram illustrating the influence of the glutaraldehyde concentration on the determination of the substance in accordance with the process of the invention.

Figure 7:
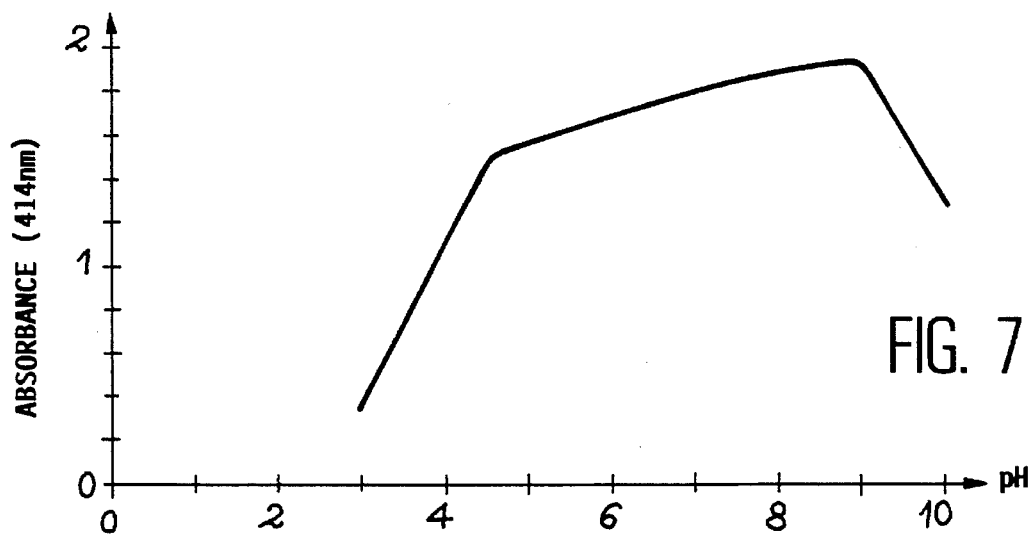

FIG. 7 A diagram illustrating the influence of the pH-value of the immobilization stage on the determination of the substance P according to the process of the invention.

Figure 8:
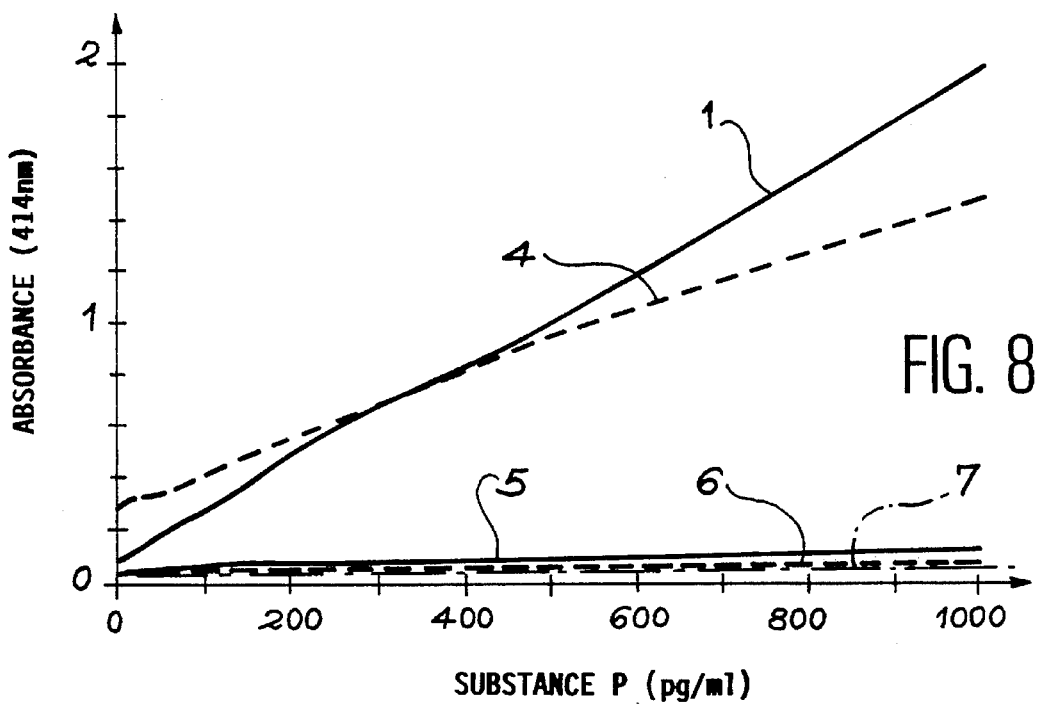

FIG. 8 A diagram illustrating the influence of the different stages of the process according to the invention on the determination of the substance P.

Figure 9:
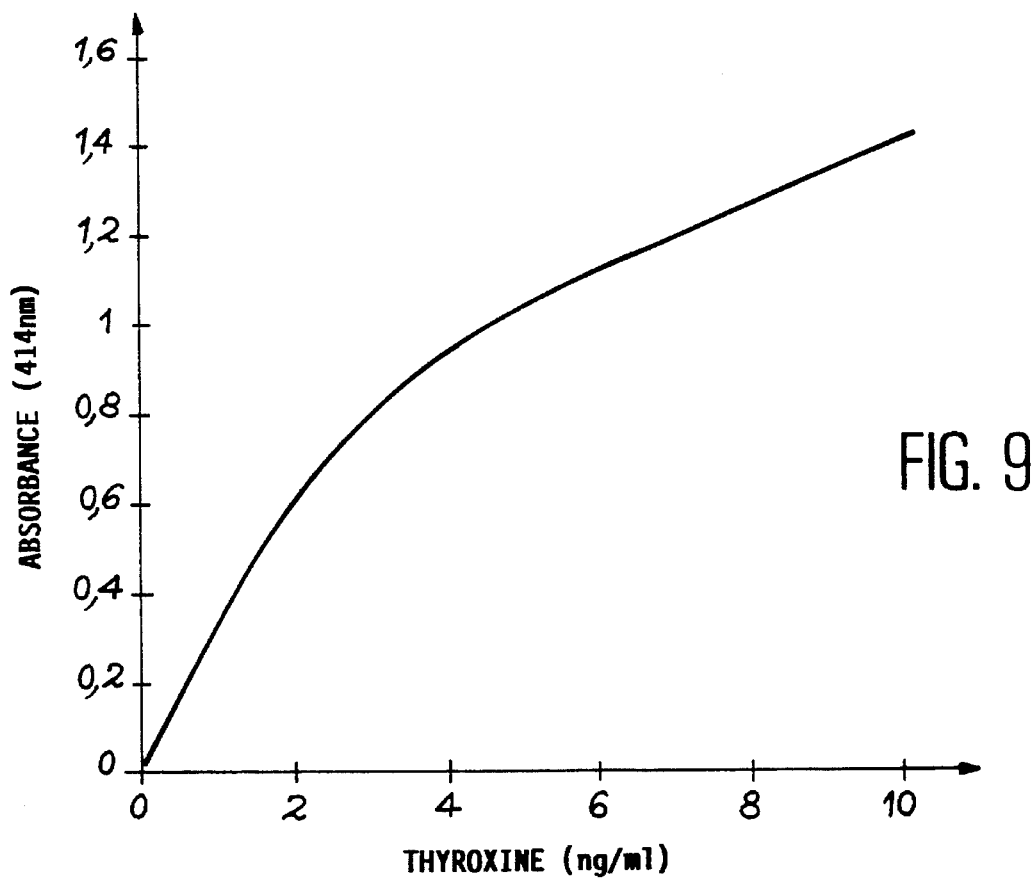

FIG. 9 A calibration curve obtained for the determination of thyroxine according to the process of the invention.

Figure 10:
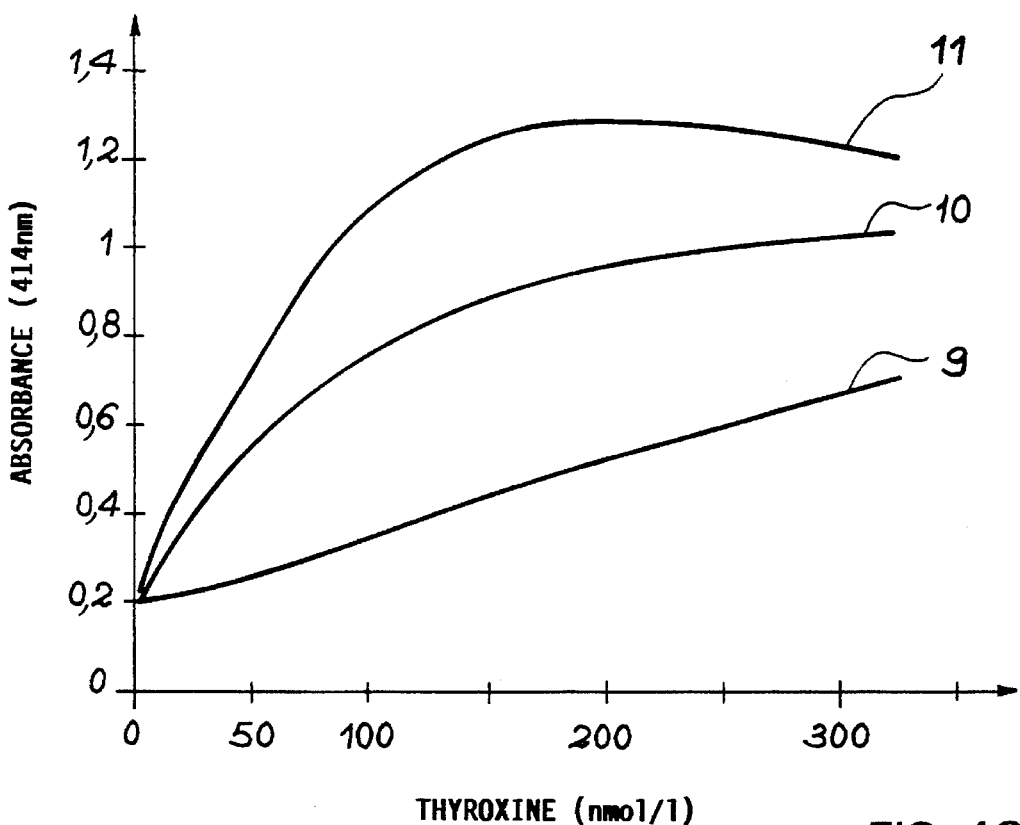

FIG. 10 The calibration curves obtained for determinations of thyroxine according to the process of the invention.

Figure 11:
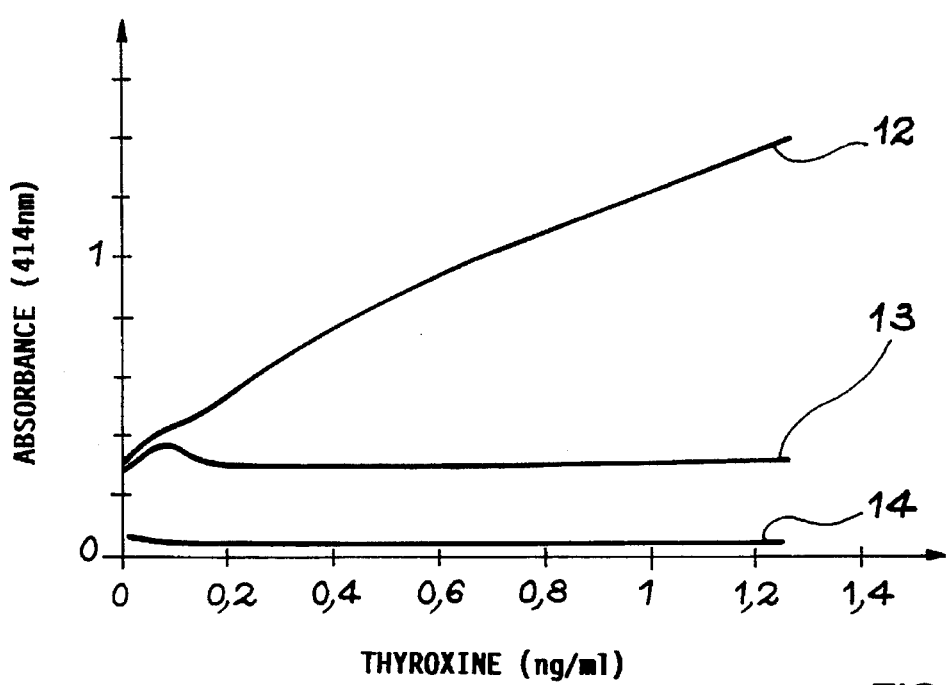

FIG. 11 A diagram illustrating the influence of the different stages of the process according to the invention on thyroxine determination.

FIGS. 1A to 1E show the different stages of the immunometric determination process according to the invention.

Thus, FIG. 1A shows the first stage, where it is possible to see a solid phase (1) on which are fixed a capture antibody (2) specific to the substance to be determined (3) and the saturation substance (6) generally constituted by proteins such as bovine serum albumin. In order to carry out this stage, contacting takes place between the support (1) provided with its capture antibodies (2) and the saturation substance (6) with the substance to be determined (3) in order to immunologically bond said substance (3) to the fixed antibody (2). The antibody quantity fixed to the solid phase corresponds to an excess compared with the quantity of the substance to be determined present in the sample.

Figure 1B:
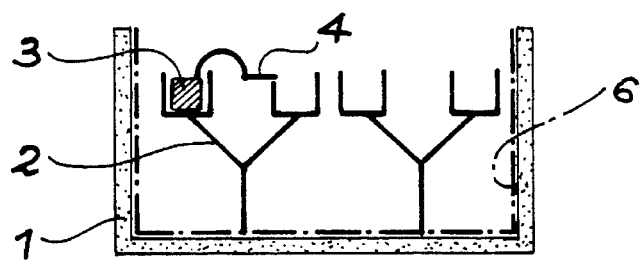
Figure 1C:
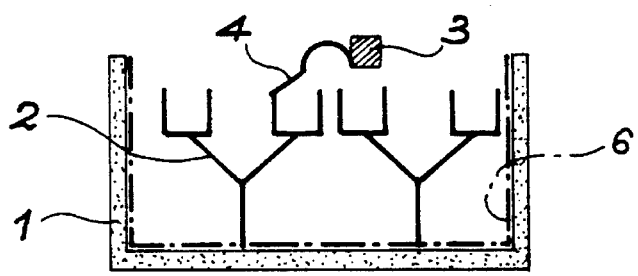

In the second stage, whereof two parts are shown in FIGS. 1B and 1C, the solid phase undergoes a treatment by means of an at least bifunctional reagent in order to immobilize the substance to be determined (3) by the formation of a covalent bond (4) on the solid phase (1) (FIG. 1B). This covalent bond can be directly established with the solid phase, with the first capture antibody and/or with the saturation substance.

In the second part, the epitope of the substance to be determined (3) is rendered accessible with a view to a further immunological reaction whilst denaturing its immunological bond with the antibody (2).

In order to carry out the first immobilization part, contacting takes place between the solid phase (1) on which are fixed the saturation substance, the capture antibody (2) and the substance to be determined (3) immunologically bonded to said antibody, with a solution of an at least bifunctional reagent having an appropriate pH and accompanied by stirring for an adequate time.

The pH is more particularly dependent on the polyfunctional reagent used. Thus, in the case of glutaraldehyde, preference is given to a pH between 5 and 9, whereas in the case of disuccinimidyl suberate (DSS), preference is given to a pH of 7 to 9. These pH-values are obtained by means of appropriate buffers.

In order to stop the reaction, it is then possible to add a stopping solution, whose function is either to destroy the existing functional groups able to react with the bifunctional reagent, or react with the free functional groups of the bifunctional reagent. Thus, when using as the bifunctional reagent glutaraldehyde, the stopping solution can comprise a reducing agent such as $NaBH_4$, in order to destroy the excess aldehyde functions of the glutaraldehyde, or an amine such as ethanol amine in order to use the remaining groups of the glutaraldehyde able to react with the amine functions.

In the second part (FIG. 1C), there is a denaturation treatment of the immunological bond of the substance to be determined with the first antibody. This denaturation treatment can take place in conventional manner using appropriate reagents, or under the action of ultrasonics or heat.

For example, these reagents can be chosen from among acids such as HCl, bases such as NaOH, organic solvents, e.g. alcohols such as methanol, surfactants and mineral salts. The reagent used is chosen as a function of the antigen-antibody pair and the nature of the bond between the first antibody and the solid phase.

In certain cases, there is no need to perform this second denaturation, because it can be simultaneously obtained in the first immobilization part, as a result of the reaction conditions used.

Figure 1D:
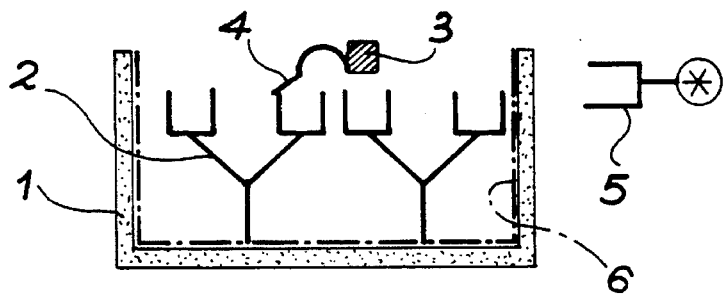
Figure 1E:
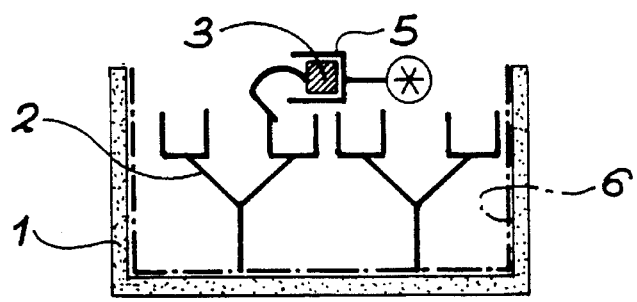

In the third stage shown in FIG. 1D, contacting takes place between the solid phase (1) on which is immobilized the substance to be determined (3) by a covalent bond (4) with a second labelled antibody (3) specific to the substance (3). This takes place by means of a solution containing a labelled antibody quantity corresponding to an excess compared with the quantity of immobilized substance to be determined.

In the fourth stage (FIG. 1E) measurement takes place of the quantity of labelled antibody (5) fixed to the solid phase by immunological bonding with the substance to be determined (3). This measurement is performed by conventional methods such as those conventionally used for this type of determination and as a function of the marker used.

In order to obtain the calibration curve, several determinations take place on standard solutions having known concentrations of the substance to be determined and whilst operating under the same conditions, which gives fixed antibody levels corresponding to the different concentrations with a view to plotting the curve.

This is followed by the determination of a sample having an unknown concentration under the same conditions and whilst referring to the calibration curve. On the basis of the measurement of the quantity of the second fixed antibody, the concentration of the substance to be determined of the sample is obtained.

It is pointed out that each stage of the process is preceded by a conventional washing operation, carried out by means of washing buffers.

Hereinafter a description is given of determinations performed according to the invention.

EXAMPLE 1

Determination of the substance P

In this example the solid phase is constituted by a microtitration plate having 96 cavities and made from polystyrene, to which is fixed an antisubstance P monoclonal antibody constituted by antibody SP14 described by Couraud et al, in J. of Neurochemistry, vol. 49, No. 6, 1987, pp 1708–1718 and operating in the following way.

To each cavity are added 200 µl of $5.10^{-2}M$ (pH 7.4) phosphate buffer containing 10 µg/ml of antisubstance P antibody (SP14) and incubation is allowed to take place for 18 h at 22° C. Each cavity is then washed with a washing buffer constituted by the previously used phosphate buffer, which also contains 0.05% of Tween 20, followed by the addition to each cavity of 300 µl of buffer EIA, which is a 0.1M (pH 7.5) potassium phosphate buffer containing 0.1 mole/l of NaCl, 1 mmole/l of ethylene diamine tetraacetic acid (EDTA), 0.1% of bovine serum albumin (BSA) and 0.01% of sodium nitride, in order to saturate the solid phase with a saturation substance (BSA). The plates are maintained at 4° C. for at least 24 h prior to the first use.

This is followed by the first stage of the determination by introducing into each cavity, following the washing with the washing buffer, of a standard solution of substance P or the sample, at a rate of 100 µl in the IEA buffer. Incubation is allowed to take place for 18 h at +4° C., followed by washing using the washing buffer.

This is followed by the second stage in two parts. In the first part, addition takes place to each cavity of 100 µl of 0.1M (pH 9) borate buffer containing 2.5% glutaraldehyde and reaction is allowed to take place for 1 h accompanied by moderate stirring. After washing, addition takes place to each cavity of 250 µl of a stopping solution constituted by a 4 mg/ml sodium berohydride solution and reaction is allowed to take place for 1 h, followed by washing with the washing buffer.

In the second part, addition takes place of 250 µl of 0.1N HCl and reaction is allowed to take place for 10 min at 22° C. As a result denaturation takes place of the immunological bend between the substance P (3) and the first antibody (2) in order to render accessible the epitope of the substance P with a view to a further immunological reaction.

Following washing, the third stage is performed by adding to each cavity 200 ul of the antisubstance P monoclonal antibody used in the first stage and labelled with acetylcholinesterase (ACHE) (5EU/ml) and which is diluted in buffer EIA and incubation is allowed to take place for 18 h at 4° C., followed by a washing.

In order to carry out the fourth stage, i.e. measure the quantity of the second antibody (5) fixed to the solid phase, measurement takes place of the enzymatic activity by adding to each cavity 200 µl of Ellman reagent, constituted by a mixture of acetyl thiocholine and DTNB, as described by Pradelles et al in Anal. Chem., *57, 1985*, p 1170, the enzymatic reaction being performed for 1 h, followed by the determination of the absorbance at 414 nm. On the basis of the absorbance measurements obtained for the standard solution, the calibration curve is plotted and is shown in FIG. 2, which gives the substance P concentration (in pg/ml) as a function of the absorbance at 414 nm.

On the basis of the absorbance obtained in the cavity containing the sample, it is possible to establish the substance P concentration of the sample by referring to the calibration curve of FIG. 2.

Thus, the process of the invention permits a precise, sensitive determination of substance P, the detectable concentration being 6 pg/ml.

Comparative Example 1

Determination of the substance P

This example uses the method of determination by competition and the same monoclonal antibody SP14 as in example 1 for determining substance P.

In this case, use is made of a microtitration plate and monoclonal antibody SP14 operating in the manner described by Couraud et al in J. of Neurochemistry, vol. 49, No. 6, 1987, p 1708–1718. This is followed by the introduction into each cavity of 50 µl of standard solution or sample and 50 µl of the conjugate substance P-acetyl cholinesterase serving as the enzymatic tracer. After incubation for one night at 4° C., the plates are washed and the immobilized enzymatic activity is determined proceeding in the manner described in example 1.

This gives the calibration curve shown in FIG. 3, on which is plotted on the ordinate the ratio $B/B_O$ (in %) as a function of the concentration of substance P (in ng/ml). It is pointed out that B represents the measured absorbance in the presence of substance P and $B_O$ the measured absorbance in the absence of substance P.

FIG. 4 illustrates the precision profiles obtained in the determination of example 1 (curve 1) and the determination of the comparative example 1 (curve 2). These precision profiles represent the variations of the precision coefficient CV (in %) as a function of the quantity of substance P (in pg/ml) in logarithnic coordinates.

In order to plot these curves, eight measurements are performed for each concentration of substance P in the standard solution in order to determine the standard deviation d and the mean value $v_m$ relative to each concentration. The precision coefficient CV (in %) is evaluated on the basis of these measurements by the formula:

$$CV = \frac{d}{v_m} \times 100$$

FIG. 4 also shows that the precision coefficient and the sensitivity are better in the case of curve 1 and that the precision coefficient is in particular very good in the concentration range from 30 to 1000 pg/ml.

FIG. 5 shows the absorbance as a function of the concentration of substance P in the case of the determination of example 1 (curve 1) and in the case of the determination of the comparative example 1 (curve 2).

These results show that the detection limit (LDD) is approximately 10 pg/ml in the case of the determination according to the invention, whereas it is approximately 900 pg/ml in the case of the determination by competition according to the prior art.

Thus, the immunometric determination process according to the invention permits a precise, sensitive determination of substance P. In particular, it makes it possible to attain a greater precision and to detect smaller quantities of substance P.

EXAMPLE 2

Determination of substance P

This example studies the influence of the concentration of glutaraldehyde used in the second stage of immobilizing the substance P on the results of the determination. In this case determinations take place as in example 1 on a standard solution containing 500 pg/ml of substance P and using glutaraldehyde concentrations between 0 and 2.5%, the absorbance being measured at 414 nm in each case.

The results obtained are given in FIG. 6, which represents the absorbance at 414 nm as a function of the glutaraldehyde concentration. It can be seen that the absorbance increases with the glutaraldehyde concentration and that good results are obtained in the concentration range between 0.5 and 2.5%.

EXAMPLE 3

Determination of substance P

This examples studies the influence of the pH used during the immobilization stage, i.e. the pH of the glutaraldehyde solution on the determination.

The operating procedure of example 1 is followed on a standard solution of 500 pg/ml of substance P using during the immobilization stage pH-values between 3 and 10.

FIG. 7 shows the evolution of the absorbance as a function of the pH used. Thus, it can be seen that the absorbance is better in the pH range from 5 to 9.

EXAMPLES 4 TO 7

Determination of the substance P

These examples study the influence of the two parts of the second stage of the process according to the invention on the determination. All these examples follow the operating procedure of example 1, apart from the following modifications to the second part.

In example 4, $NaBH_4$ is not used, i.e. no immobilization reaction stopping solution is used.

In example 5 no glutaraldehyde solution is used, the reduction stage being performed by $NaBH_4$.

In example 6 the immobilization stage is completely eliminated, i.e. the reaction with the glutaraldehyde solution and the addition of the stopping solution.

In example 7 the immobilization stage is performed, but not the stage of releasing the epitope by the hydrochloric acid solution.

These modifications are grouped in the following table.

TABLE 1

| Stage 2 | | Ex 1 | Ex 4 | Ex 5 | Ex 6 | Ex 7 |
|---|---|---|---|---|---|---|
| Part 1 | Glutaral-dehyde | yes | yes | no | no | yes |
|  | $NaBH_4$ | yes | no | yes | no | yes |
| Part 2 | HCl | yes | yes | yes | yes | no |

The results obtained are given in FIG. 8, which represents the calibration curves obtained in each case, i.e. the evolution of the absorbance at 414 nm, as a function of the concentration of substance P (pg/ml).

In FIG. 8, curve 1 refers to example 1, curve 4 to example 4, curve 5 to example 5, curve 6 to example 6 and curve 7 to example 7.

FIG. 8 makes it clear that the performance of the substance P immobilization stages on microtitration plates and the release of its epitope are essential for permitting the determination of substance P.

EXAMPLE 8

Determination of thyroxine

For this determination use is made of a microtitration plate having 96 cavities identical to that of example and in said cavities is fixed an antithyroxine antibody constituted by a monoclonal antibody from Institut pasteur and whilst operating under the sane conditions as in example 1.

Into each cavity is then introduced a standard thyroxine solution at a rate of 100 µl in a 0.05M (pH 8.6) barbital buffer containing 0.1% BSA, followed by incubation for 1 h at 22° C. Washing then takes place with the aid of the washing buffer used in example 1.

In the second stage, to each cavity are added 100 ul of 0.1M (pH 7) phosphate buffer and 10 µl of disuccinimidyl suberate (DSS) at a concentration of 1 mg/ml in a mixture of dimethyl formamide and n-propanol (1/9 by volume) and reaction takes place for 15 min at 22° C. This is followed by washing with the washing buffer and the stopping of the reaction with 0.1M ethanolamine in the 0.1M (pH 9) borate buffer. After washing, addition takes place of 250 µl of 0.1N soda to each cavity in order to release the epitope from the thyroxine.

After washing, addition takes place of 100 µl of the same antithyroxine monoclonal antibody labelled with acetyl cholinesterase (ACHE) (5 EU/ml) diluted in the barbital buffer and incubation takes place for 1 h at 22° C.

After washing, Ellman reagent (200 µl) is added and the enzymatic reaction is allowed to continue for 10 min and then the absorbance is measured at 414 nm.

The results obtained, i.e. the calibration curve, are given in FIG. 9, which represents the evolution of the absorbance at 414 nm, as a function of the thyroxine concentration (ng/ml). The detection limit is 61 pg/ml.

Thus, a high sensitivity is obtained using a single antibody and improving the specificity of the determination by the use of a monoclonal antibody.

For comparison purposes, it is pointed out that the same determination performed by competition with the sane antibody gives a detection limit of 1 ng/ml.

EXAMPLES 9 TO 11

Thyroxine determinations

For these determinations, the same operating procedure as in example 8 is followed using different agents for inhibiting the action of bonding proteins, such as TBG, and adding 10 µl of standard plasma or sample, either to 100 ul of barbital buffer (example 9), or to 100 µl of barbital buffer containing 1 mg/ml of ANS (8-anilino-2-naphthalene sulphonic acid) (example 10), or to 100 µl of barbital buffer containing 0.4% of thymerosal (example 11).

This is followed by the thyroxine immobilization stage in the cavities using a 2.5% glutaraldehyde solution in the borate buffer, which is then reacted for 30 min and under moderate stirring. The reaction is then stopped using $NaBH_4$, followed by 30 min reaction.

For the release of the epitope and the remainder of the determination stages, the procedure of example 8 is used.

The results obtained are given in FIG. 10, which represents the calibration curves obtained, namely the absorbance at 414 nm as a function of the thyroxine concentration (in nmole/l).

In FIG. 10 curve 9 refers to example 9, curve 10 to example 10 and curve 11 to example 11.

On the basis of FIG. 10, it can be seen that the best results are obtained when the barbital buffer is used with thymerosal.

EXAMPLES 12 TO 14

Thyroxine determinations

In these examples, the influence of the different stages of the process to the invention on the determination is studied. All these examples follow the same operating procedure as in example 8, apart from the following modifications.

Example 12 uses DSS as the immobilization reagent, ethanol amine as the stopping solution and 0.1N hydrochloric acid as the epitope release reagent.

In example 13 the thyroxine immobilization stage is performed by DSS and ethanol amine, but the epitope is not released by HCl.

In example 14 there is no thyroxine immobilization stage or epitope release stage.

The results obtained are shown in FIG. 11, which gives the calibration curves obtained. In FIG. 11 curves 12, 13, 14 relate respectively to examples 12, 13 and 14.

On the basis of FIG. 11, it can be seen that the two immobilization and epitope release stages are essential to permit thyroxine determination, because there is no absorbance variation as a function of the thyroxine concentration in examples 13 and 14.

Therefore the process of the invention is very interesting, because it permits the obtaining of a high sensitivity using a single antibody. Moreover, the results given in the following table 2 of correlation studies performed on substance P from different sources, have demonstrated that when using the process of the invention results equivalent to those of a determination by competition using the same antibody are obtained, which confirms the reliability of the process according to the invention.

TABLE 2

| Origin of substance P | Determination according to the invention SP (ng/ml) | Determination by competition SP (ng/ml) |
| --- | --- | --- |
| Rat brain extract | 70 | 75.5 |
| Rat spinal Moelle extract | 61.4 | 61.3 |
| Mouse brain extract | 75.5 | 70 |
| Mouse spinal Moelle extract | 33.4 | 32.1 |

I claim:

1. A process for the immunometric determination of an antigen or hapten, comprising:

contacting a sample containing said antigen or hapten with a solid phase on which are fixed a saturation substance and a first antibody specific to a single epitope of said antigen or hapten, to immunologically bind said antigen or hapten to said first antibody fixed to said solid phase, immobilizing said antigen or hapten to said first antibody fixed to said solid phase by reacting with a reagent which forms one or more covalent bonds between said antigen or hapten and said first antibody fixed to said solid phase, denaturing the immunological bond between said antigen or hapten and said first antibody fixed to said solid phase, contacting said antigen or hapten having one or more covalent bonds to said first antibody fixed to said solid phase with a second, labelled antibody specific to the same epitope of said antigen or hapten, to immunologically bind said second, labelled antibody to said antigen or hapten having one or more covalent bonds to said first antibody fixed to said solid phase, measuring the quantity of said second, labelled antibody immunologically bound to said antigen or hapten, and determining on a calibration curve the quantity of said antigen or hapten on the basis of the quantity of said second, labelled antibody immunologically bound to said antigen or hapten.

2. The process of claim 1, wherein said reagent which forms one or more covalent bonds is a bifunctional reagent.

3. The process of claim 2, wherein said bifunctional reagent is glutaraldehyde or disuccinimidyl suberate.

4. The process of claim 1, wherein said denaturing comprises treating said antigen or hapten immobilized to said first antibody fixed to said solid phase with an acid, a base, an organic solvent, a surfactant or a mineral salt.

5. The process of claim 1, wherein said denaturing comprises heating or irradiating with ultrasonic irradiation.

6. The process of claim 1, wherein each of said first antibody and said second, labelled antibody is a monoclonal antibody.

7. The process of claim 1, wherein said second, labelled antibody is labelled with a radioactive element, an enzyme, a fluorescent marker, a luminescent marker or a molecule able to react with avidin or streptavidin.

8. The process of claim 1, wherein said antigen or hapten is substance P or thyroxine.

9. The process of claim 1, wherein said antigen or hapten is a hapten selected from the group consisting of ACTH, angiotensin, ANF, bradykinin, encephalin, LHRH, oxytocin, vasopressin, a neurokinin, endotheline and leucotriene $E_4$.

10. The process of claim 1, wherein said antigen or hapten is a monoepitopic antigen or hapten.

11. The process of claim 1, wherein said saturation substance is bovine serum albumin.

12. A process for the immunometric determination of an antigen or hapten, consisting essentially of:

contacting a sample containing said antigen or hapten with a solid phase on which are fixed a saturation substance and a first antibody specific to a single epitope of said antigen or hapten, to immunologically bind said antigen or hapten to said first antibody fixed to said solid phase, immobilizing said antigen or hapten to said first antibody fixed to said solid phase by reacting with a reagent which forms one or more covalent bonds between said antigen or hapten and said first antibody fixed to said solid phase, denaturing the immunological bond between said antigen or hapten and said first antibody fixed to said solid phase, contacting said antigen or hapten having one or more covalent bonds to said first antibody fixed to said solid phase with a second, labelled antibody specific to the same epitope of said antigen or hapten, to immunologically bind said second, labelled antibody to said antigen or hapten having one or more covalent bonds to said first antibody fixed to said solid phase, measuring the quantity of said second, labelled antibody immunologically bound to said antigen or hapten, and determining on a calibration curve the quantity of said antigen or hapten on the basis of the quantity of said second, labelled antibody immunologically bound to said antigen or hapten.

* * * * *